United States Patent [19]

Burke et al.

[11] Patent Number: 4,876,277
[45] Date of Patent: Oct. 24, 1989

[54] ANTIMICROBIAL/ANTIFUNGAL COMPOSITIONS

[75] Inventors: Basil A. Burke, Palo Alto, Calif.; Muraleedharan G. Nair, East Lansing, Mich.

[73] Assignee: Plant Cell Research Institute, Inc., Dublin, Calif.

[21] Appl. No.: 55,737

[22] Filed: May 29, 1987

[51] Int. Cl.$^4$ .................. C07D 317/64; C07D 317/46
[52] U.S. Cl. ..................................... 514/465; 514/464; 549/437
[58] Field of Search ............... 514/465, 464; 549/445, 549/437

[56] References Cited

U.S. PATENT DOCUMENTS 3,812,262  5/1974  Chodnekar et al. ............... 514/464

FOREIGN PATENT DOCUMENTS 128129  10/1970  India .

OTHER PUBLICATIONS

Dallacker et al., Chem. Abs., 99, 105157d, (1983).
Nair et al., "Insecticidal Properties of Some Metabolites of Jamaican Piper spp., and the Amides Synthesized from 5,6-Z and E-Butenolides of Piper fadyenii", in Agric. Biol. Chem., 50, pp. 3053–3058, (1986).
Devakumar et al., "New Sesamol Ethers as Pyrethrum Synergists", in Agric. Biol. Chem., 49, pp. 725–730, (1985).
Burke et al., "Phenylpropene, Benzoic Acid and Flavanoid Derivatives from Fruits of Jamaican Piper Species" in Phytochem., 25, (1986).
Homans et al., "Direct Bioautography on Thin-Layer Chromatograms as a Method for Detecting Fungitoxic Substances" in J. Chromatog., 51, pp. 327–329, (1970).
Dallacker, "Zur Synthese von Dimethoxy-Methylendioxy-Allylbenzolen" in Chem. Ber., 102, pp. 2663–2676, (1969).
Nair, "Chemical and Preliminary Biological Investigation of Some Jamaican Medicinal Plants", Thesis, May 1984.

Primary Examiner—John W. Rollins
Assistant Examiner—W. Catchpole
Attorney, Agent, or Firm—Jacques M. Dulin

[57] ABSTRACT

Substituted olefinic (allyl) benzene compounds which exhibit important antimicrobial (antibacterial and antifungal) activity, compositions and methods of delivery against pathovars and pathogens, and methods of synthesis from commonly available reactants. The antifungal composition active ingredient is one or more 4,5-substituted 2,3-alkylidenedioxy-1-olefinic benzenes of the formula:

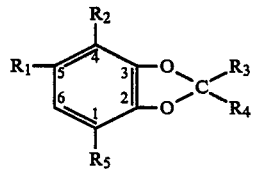

Formula I where $R_1$ and $R_2$ may be the same or different, and are selected from OH, and $C_1$–$C_5$ alkoxy (—OR) or thioalkyl (—SR) groups. $R_3$ and $R_4$ are selected from H and $C_1$–$C_5$ alkyl, alkenyl and alkynyl groups, and $R_5$ is selected from $C_3$–$C_7$ alkyl, alkenyl and alkynyl groups. The preferred compounds are 4,5-substituted-2,3-methylenedioxy-1-allyl benzenes. Where $R_1$=OCH$_3$, $R_2$=OH, $R_3$ and $R_4$=H and $R_5$=allyl (2',3' propenyl) the compound may be called nor methyl-pseudo-dillapiole. Where $R_1$=$R_2$=OCH$_3$, $R_3$ and $R_4$ are again H, and $R_5$=allyl, the compound may be called pseudo-dillapiole. Compositions including these compounds exhibit antimicrobial activity against a variety of pathogens and pathovars, e.g., Xanthomonas campestris spp. bacteria, antifungal activity against a variety of fungi and bacteria, and are highly specific, e.g., antifungal activity against wheat powdery mildew, but do not affect seed germination or have herbicidal or insecticial activity. Methods and compositions for delivery of these agents against such pathogens, and methods of chemical synthesis of the compounds are disclosed.

18 Claims, No Drawings

ANTIMICROBIAL/ANTIFUNGAL COMPOSITIONS

FIELD

This application relates to substituted olefinic benzene compounds which exhibit important antimicrobial and antifungal activity, compositions and methods of delivery against pathovars and pathogens, and methods of synthesis from commonly available reactants.

More particularly, this application relates to 4,5-substituted 2,3-alkylidenedioxy-1-olefinic benzenes of the formula:

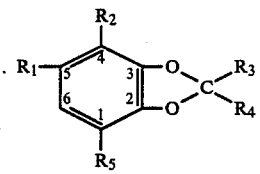

Formula I wherein $R_1$ and $R_2$ may be the same or different, and are selected from OH, and $C_1$-$C_5$ alkoxy (—OR) or thioalkyl (—SR) groups, $R_3$ and $R_4$ are selected from H and $C_1$-$C_5$ alkyl, alkenyl and alkenyl groups, and $R_5$ is selected from $C_3$-$C_7$ alkyl, alkenyl and alkynyl groups. The preferred compounds are 4,5-substituted-2,3-methylenedioxy-1-allyl benzenes. Where $R_1$=OCH$_3$, $R_2$=OH, $R_3$ and $R_4$=H, and $R_5$=allyl (2',3' propenyl) the compound may be called nor methyl-pseudo-diallapiole Where $R_1$=$R_2$=OCH$_3$, and $R_3$ and $R_4$ are again H and $R_5$=allyl, the compound may be called pseudo-dillapiole. These compounds exhibit antimicrobial activity against a variety of pathogens and pathovars, e.g., *Xanthomonas campestris* spp. bacteria, antifungal activity against a variety of fungi and bacteria, and are highly specific, e.g., antifungal activity against wheat powdery mildew but do not affect seed germination or have significant herbicidal or insecticidal activity. The invention is also directed to methods and compositions for delivery of these agents against such pathogens and to methods of chemical synthesis of the compounds.

BACKGROUND

Dallacker [1] reports the synthesis of dimethoxy-methylenedioxy-allylbenzenes including pseudo-dillapiole (Dallacker's pseudo-dillapiole compound 8f, 4,5-dimethoxy-2,3-methylenedioxy-1-allyl-benzene) and nor pseudo-dillapiole (Dallacker's compound 8e, 6-methoxy-2,3-methylenedioxy-4-allyl-phenol) two of the dimethoxy compounds encompassed in Applicants' genus. Dallacker also shows a number of position isomers of some of Applicants' compounds, including dillapiole (Dallacker's "Dill Apiole", 2,3-Dimethoxy-4,5-methylenedioxy-allyl-benzene), apiole (Dallacker's compound 7, 5,6-dimethoxy-2,3-methylenedioxy-allyl-benzene), 2,5-dimethoxy-3,4-methylenedioxy-allyl-benzene (Dallacker's "Petersilen-Apiol"), 4,6-dimethoxy-2,3-methylenedioxy-allyl-benzene (Dallacker's compound 4i), and 2,6-dimethoxy-3,4-methylenedioxy-allyl-benzene (Dallacker's compound 5i). Dallacker also shows monomethoxy, allyloxy, hydroxy (allyl-phenol), nitro, amino, acetamino, and propenyl derivatives.

However, Dallacker neither shows nor suggests any biological activity, much less antimicrobial or antifungal properties.

Several methylenedioxyphenyl compounds and the compound dillapiole 5,6-dimethoxy-3,4-methylenedioxy-1-allyl benzene, were reported by Devakumar, et al. [2], and in an Indian patent [3], No. 128,129 (1969) to have synergic activity with pyrethrum insecticides.

In the provisional specification of the Indian patent No. 128,129 attention was focused on the propyl analog of dillapiole because of undesirable physiologic side effects of the allyl side chain. The allyl side chain was hydrogenated in the presence of a Raney-nickel catalyst, and the resulting di-hydrogenated compound was found to be an effective synergic with pyrethrins against houseflies, cockroaches and flour beetles.

Citrus Canker is a deadly plant disease caused by *Xanthomonas campestris pv. citrii*. This disease causes millions of dollars damage to citrus crops in the work each year, adversely affecting the world food supply. Currently, the only solution is containment by isolation/removal of the diseased plants, followed by burning the groves. A recent newspaper article (S. F. Chronicle Feb. 18, 1986, p. 17) reports that a serum of "old beer and bacteria" developed by RAM Chemical of Borger TX is claimed to be 100% effective in stopping outbreaks of canker.

Wheat powdery mildew (WPM) is a fungal pathovar, *Erysiphe graminis*, that causes extensive damage to wheat crops. A variety of compounds are used to combat these diseases. For example, wheat is treated with duPont's BENOMYL, methyl 1-(butylcarbamoyl)-2-benzimidazolecarbonate, Farbenfabriken Bayer's EDIFENPHOS, O-ethyl-S,S-diphenyl-dithiophosphate, and Bayer AG/Mobay Chemical Company's BAYLETON, 1-(4-chlorophenoxy)-3,3-dimethoxy-1-(1H-1,2,4-triazol-1-yl)-2-butanone. However, the Edifenphos cannot be sold or used in the U.S., is toxic to fish, should not be mixed with alkaline materials, and cannot be used within 10 days before or after a propanil application. Benomyl is likewise toxic to fish, livestock may not be grazed on treated areas, it should not become wet during storage or combined with alkaline pesticides and apples do not express fine fruit finish. Bayleton exhibits some plant stunting and deformation on ornamentals when used at excessive rates and is toxic to fish.

There is thus a need for new compounds which are effective against such plant diseases.

THE INVENTION

Objects:

It is among the objects of the invention to provide a new class of compounds having antimicrobial properties, more specifically antifungal and antibacterial properties.

It is another object of the invention to provide 4,5 substituted 2,3-alkylidenedioxy 1-olefinic benzenes which have antibacterial and/or antifungal properties.

It is another object of the invention to provide compositions and methods of delivery of the compounds of this invention to combat bacterial and fungal pathogens and pathovars, more particularly *Xanthomonas campestris* and *Erysiphe graminis*.

It is another object of this invention to provide methods of synthesizing the compounds of this invention.

Still other objects will be evident from the summary, detailed description and claims.

SUMMARY

We have discovered that 4,5-substituted-2,3-alkylidenedioxy-1-olefinic-benzene compounds exhibit important antimicrobial and antifungal activity. More specifically the class of compounds are 4,5-substituted 2,3-alkylidenedioxy-1-olefinic benzenes of the formula:

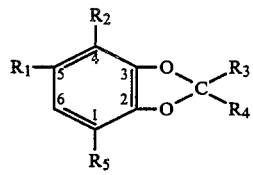

Formula I where $R_1$ and $R_2$ may be the same or different, and are selected from OH, and $C_1$–$C_5$ alkoxy (—OR) or thioalkyl (—SR) groups, $R_3$ and $R_4$ are selected from H and $C_1$–$C_5$ alkyl, alkene and alkyne groups, and $R_5$ is selected from $C_3$–$C_7$ alkane, alkene and alkyne groups. The preferred compounds are 4,5-substituted-2,3-methylenedioxy-1-allyl benzenes. Where $R_1$=$OCH_3$, $R_2$=OH, $R_3$ and $R_4$=$H_1$ and $R_5$=allyl (2',3' propenyl) the compound may be called nor methyl-pseudo-dillapiole. Where $R_1$=$R_2$=$OCH_3$, $R_3$ and $R_4$ are again H, and $R_5$=allyl, the compound may be called pseudo-dillapiole These compounds exhibit antimicrobial activity against a variety of pathogens and pathovers, e.g., *Xanthomonas campestris pv. carotae* and *pv. campestris*, pathovars which are closely related to the bacteria *xanthomonas campestris pv. citrii* the causative agent of citrus canker. The compounds also show antifungal activity against a variety of fungi and bacteria, and are highly specific, e.g., antifungal activity against wheat powdery mildew, but do not affect seed germination or have significant herbicidal or insecticidal activity. The invention is also directed to methods and compositions for delivery of these agents against such pathogens and to methods of chemical synthesis of the compounds.

The $R_5$ sidechain may be saturated or unsaturated. It is presently preferred to be unsaturated and to have a terminal double bond. Thus, where $R_5$ is allyl, we prefer a 2',3' double bond although a 1',2' bond may be used. Likewise, in the longer unsaturated groups, the double or triple bond may be in any desired position, e.g. in butylene at the 1',2' position, the 2',3' position or the 3',4' position.

More particularly, the 4,5 dimethoxy compound pseudo-dillapiole was found to have high activity against preventing infection of wheat by *Erysiphe graminis*, the pathogen responsible for wheat powdery mildew (herein WPM), on the order of 95% at 100 ppm compared to the following reference compounds: 0% for ROHM a& Haas's MANCOZEB (16% Mn, 2% Zn and 62% ethylenebiodithiocarbamate ion/Mn ethylenebisdithiocarbamate plus Zn ion) at up to 300 ppm; 100% for du Pont's BENOMYL in the range of 38–300 ppm; 100% for Farbenfaariken Bayer's EDIFENPHOS in the range of 75–300 ppm; 100% for Nachricten Bayer's BAYLETON in the range of 38–100 ppm; and 0% for both Nihon Nohyaku's FUJI-ONE (diissopropyl-1, 3-dithiolau-2-ylidane malonate) and Meji Sechakaisha's ORYZEMATE (3-allyl-1, 2-benzothiazole-1, 1-dioxide) at up to 300 ppm.

The pseudo-dillapiole compound was also found to be highly specific, being substantially ineffective against: *Pseudoperonospora cubensis* the pathogen of cucumber downy mildew; *Piricularia oryzae*, the pathogen of rice blast; *Pellicularia filamentosa*, the pathogen of rice sheath blight; *Phytophtora infestans*, the pathogen of tomato leaf blight; and *Puccinia recondita*, the pathogen of wheat leaf rust.

At $ED_{50}$ concentrations on the order of 10 ppm, this compound was also effective against *Xanthomonas campestris pv. carotae* and *pv. campestris* pathovars related to the bacteria *Xanthomonas campestris pv. citrii*, the causative agent of Citrus Canker disease.

The nor methyl-pseudo-dillapiole compound ($R_2$=OH, $R_1$=$OCH_3$) is effective and equally highly specific against WPM *Erysiphe graminis* on the order of 75% at 100 ppm compared to the same reference compounds, and is effective on *Xanthomonas campestris*.

Further evidence of specificity is shown by the fact that neither compound alone proved effective as an herbicide or as an insecticide. For example, the nor methyl analog was ineffective against: average dicots, pigweed, velvet leaf, average monocots, green foxtails, signal grass, southern armyworm, mexican bean beetle, southern corn rootworm, green peach aphid, two-spotted spider mite, and southern root knot nematode. Pseudo-dillapiole was ineffective against: all the above weeds for the nor methyl analog (except signal grass which was not tested), plus cockleburr, morning glory, smartweed, barnyard grass, johnson grass, yellow nutsedge and wild oat.

These compounds are also active in the range of as low as about 10–30 ppm against a range of fungi, e.g., *Cladosporium herbarum*, a saprophyte, and against *Helminthosporium carbonum*, *Alternaria brassicicola*, *Pyrenochaeta terrestris*, and *Alternaria chrysanthemi*, the pathogens of maize, cabbage, onions and chrysanthemum, respectively. In contrast they were relatively ineffective at reasonable concentration levels against *Agrobacterium tumefaciens*, *Rhizobium japonicum* and certain yeast.

The compounds are sufficiently volatile to be applicable to plants as an aerosol. Thus, they also meet the need for a relatively short effective lifetime on crops.

The compounds are synthesized from piperonal by conversion to 3,4-methylenedioxy phenol, thence to 6-methoxy-2,3-methylenedioxybenzaldehyde, thence to 6-methylenedioxy 1-allyl ether, thence to the double claisen product, 6-methoxy-2,3-methylenedioxy-4-allyl phenol, which is the nor methyl-pseudo-diallapiole compound of the invention. This many then be methylated to pseudo-dillapiole.

DETAILED DESCRIPTION OF THE BEST MODE OF CARRYING OUT THE INVENTION

The following detailed description is by way of example and not by way of limitation of the principles of this invention and has reference to the specific examples below.

The general synthetic route is shown below, where X is halogen and $R_5$ may be fully saturated.

GENERAL SYNTHETIC ROUTE

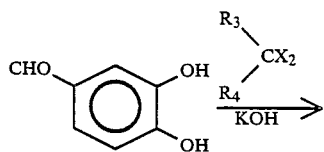

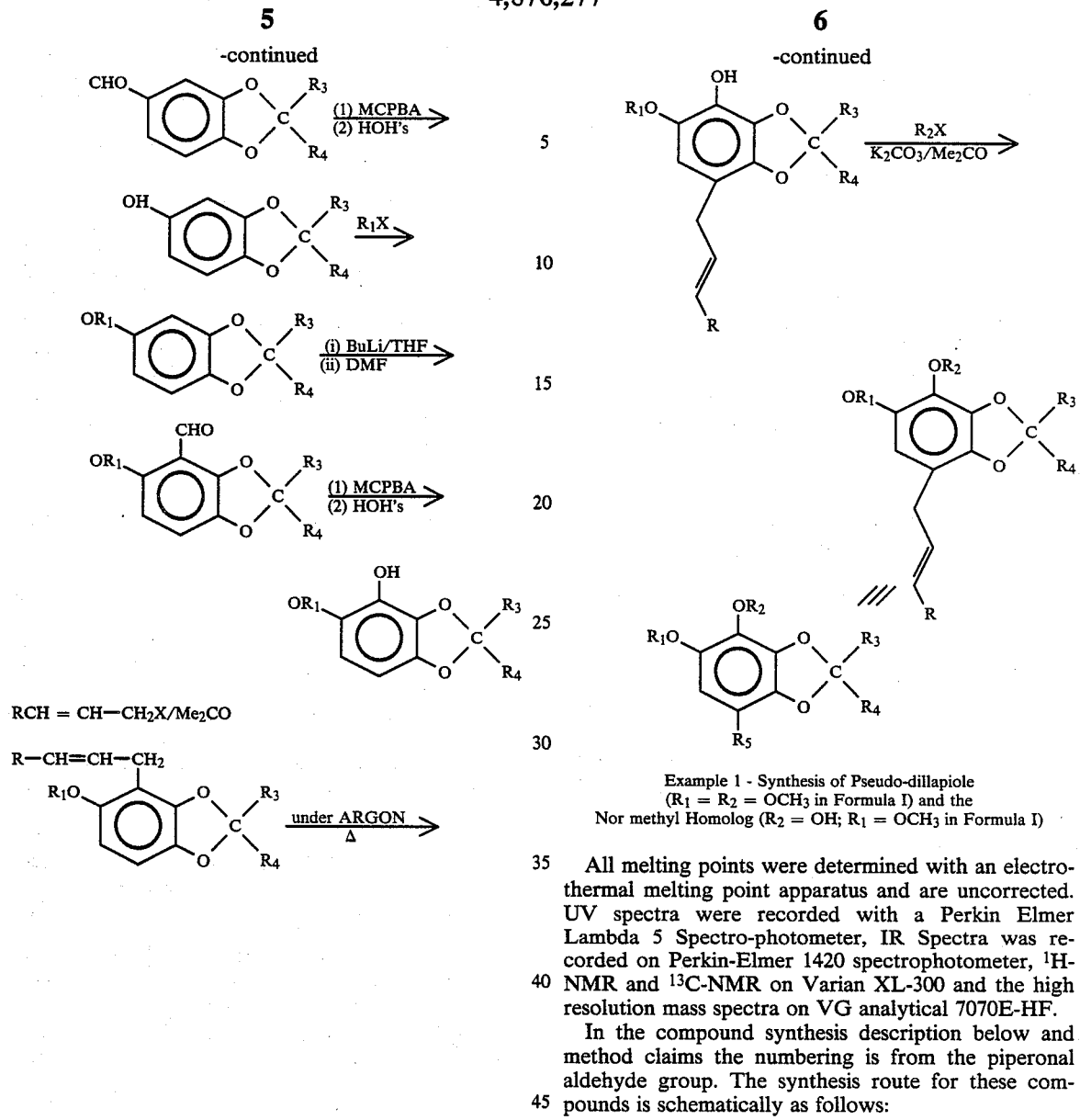

Example 1 - Synthesis of Pseudo-dillapiole
($R_1 = R_2 = OCH_3$ in Formula I) and the
Nor methyl Homolog ($R_2 = OH$; $R_1 = OCH_3$ in Formula I)

All melting points were determined with an electrothermal melting point apparatus and are uncorrected. UV spectra were recorded with a Perkin Elmer Lambda 5 Spectro-photometer, IR Spectra was recorded on Perkin-Elmer 1420 spectrophotometer, $^1$H-NMR and $^{13}$C-NMR on Varian XL-300 and the high resolution mass spectra on VG analytical 7070E-HF.

In the compound synthesis description below and method claims the numbering is from the piperonal aldehyde group. The synthesis route for these compounds is schematically as follows:

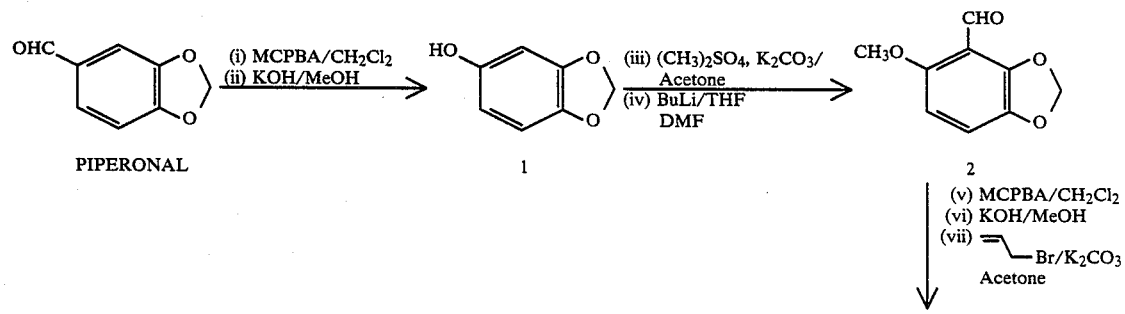

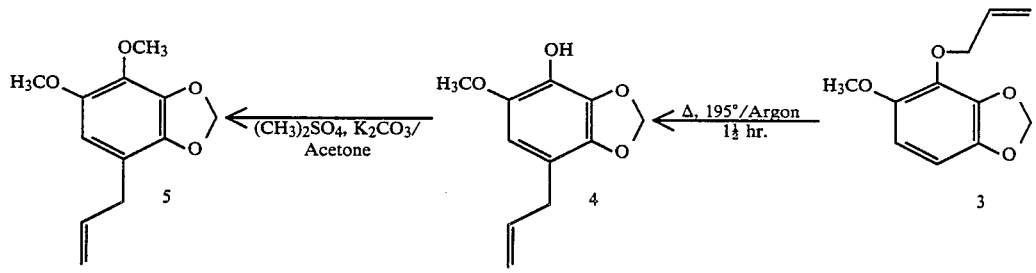

3,4 Methylenedioxy Phenol (1)

commercial piperonal (Aldrich) (60 g) was dissolved in $CH_2Cl_2$ (500 ml), m—chloroperoxybenzoic acid (MCPBA) (90 g) added in portions and left to stir at room temperature (18 hrs.). The precipitate was filtered off and washed with $CH_2Cl_2$. The combined filtrate was then washed with cold saturated $Na_2CO_3$ solution, followed by $H_2O$, dried over anhy. $MgSO_4$ and evaporated to dryness. The resulting formate ester, δ ($CDCl_3$, 300 Hz): 5.99 (2H, s, $OCH_2O$), 6.56 (1H, d, J=8 Hz, H-6), 6.65 (1H, d, J=2 Hz, H-2), 6.70 (1H, d, J=8 Hz, H-5), 8.25 (1H, s, formate), was dissolved in MeOH (250 ml) and mixed with a solution of 30 g KOH in 200 ml MeOH. The reaction mixture was left at room temp for 15 hrs., evaporated to dryness, the residue dissolved in water (300 ml), acidified to neutral by dilute HCl (6N) and extracted with ethyl acetate. The organic layer was washed with $NaHCO_3$ followed by water, dried over anhy. $MgSO_4$ and evaporated to dryness. The crude product (57 g) was recrystallized from hexane (48 g), to yield colourless crystals, mp. 54°–55° C.; IR $\nu^{max}_{KBr}$ $cm^{-1}$: 3580, 1625; UV $\nu^{max}_{MeOH}$ nm (ε): 300.1 (2436), 234.2 (2269), 215.3 (2697), with KOH in methanol 314.2 (2477), 242.6 (2781), 225.6 (2746); $^1$H-NMR δ ($CDCl_3$): 5.90 2H, s, $OCH_2O$), 6.15 (1H, dd, J=2.4, 8.0 Hz, H-6), 6.24 (1H, d, J=2.4 Hz, H-2), 6.34 (1H, d, J=8.0, Hz, H-5), 4.68 (1H, bs, exchanged with $D_2O$, phenolic); HRMS m/z: 138.0316 ($M^+$, 100, $C_7H_6O_3$), 137.0238 ($M^+$-H, 88.42, $C_7H_5O_3$).

6-Methoxy-2,3-Methylendioxy Benzaldehyde (2)

Compound 1 (47 g) in dry acetone (500 ml), $K_2CO_3$ (100 g) and dimethylsulphate (70 ml) were refluxed overnight. The white solid was filtered off, the filtrate concentrated, diluted with water and extracted with EtOAc. The EtOAc layer was washed with $NaHCO_3$ solution and water, dried over anhydrous $MgSO_4$. Removal of solvent afforded a straw coloured liquid, one spot by TLC, IR $\nu^{max}_{liq.film}$ $cm^{-1}$: 1624; UV $\nu^{max}_{MeOH}$ nm (ε): 296 (2875), 236 (2937), 217 (3027); $^1$H-NMR δ ($CDCl_3$): 3.74 (3H, s, $OCH_3$), 5.91 (2H, s, $OCH_2O$), 6.31 (1H, dd, J=2.5, 8.5 Hz, H-5), 6.49 (1H, d, J=2.5, Hz, H-1), 6.70 (1H, d, J=8.5 Hz, H-4); HRMS m/z: 152.0473 ($M^+$, 100, $C_8H_8O_3$), 137.0238 ($M^+$ —$CH_3$, 88.42, $C_7H_5O_3$). This methyl ether (40 g) in absolute THF (300 ml) at −10 C under argon gas was stirred with butyl lithium in hexane (100 ml, 1.1 mole) for 2½ hrs. After the addition of BuLi the temperature of the reaction mixture was slowly raised to room temperature. Formation of the anion was confirmed by quenching an aliquot of the reaction mixture with $D_2O$ and observing the $^1$H=NMR (disappearance of the doublet signal at 6.49 ppm). The anion thus formed was stirred with dry DMF (20 ml) in THF (100 ml), at 0° C. (10 min) followed by refluxing (2 hrs). The reaction mixture was then acidified with HCL (6N) and extracted with ether (1½ L). Drying over anhydrous $MgSO_4$ and evaporation of the solvent afforded a pale yellow crystalline compound mp 124° C., IR $\nu^{max}_{KBr}$ $cm^{-1}$: 1620, 1695, UV $\nu^{max}_{MeOH}$ nm (ε): 211 (7811), 217.9 (7788), 268 (4536), 294.6 (2177): $^1$H-NMR δ ($CDCl_3$): 3.81 (3H, s, $OCH_3$), 6.07 (2H, s, $OCH_2O$), 6.33 (1H, d, J=7 Hz, H-5), 6.88 (1H, d, J=Hz, H-4), 10.31 (1H, s, aldehyde); HRMS m/z: 180.0401 ($M^+$, 100, $C_9H_8O_4$), 165.0189 ($M^+$ —$CH_3$, 35, $C_8H_5O_4$), 137.0238 ($M^+$ —$CH_3CO$, 45, $C_7H_5O_3$).

6-Methoxy-2,3-Methylendioxy 1-Allyl Ether (3)

The aldehyde (2) (20 g) was stirred with m-chloroperoxybenzoic acid (23 g) in $CH_2Cl_2$ (500 ml) (18 hrs). The precipitate was filtered off and the filtrate washed with $Na_2CO_3$ solution, evaporated to dryness and the $^1$H-NMR of the resulting product has the chemical shifts 3.80 (3H, s, $OCH_3$), 5.95 (1H, d, J=6 Hz, C-5), 6.01 (2H, s, $OCH_2O$), 6.35 (1H, d, J=6 Hz, C-4) and 8.19 (1H, s, formate ester). The formate ester was treated with 5% KOH/MeOH at room temp (2 hr), and resulted in 12 g of a low melting solid recrystallized from hexane which has a mp of 89°–90° C.; IR $\nu^{max}_{KBr}$ $cm^{-1}$: 3530; UV $\nu^{max}_{MeOH}$ nm (ε): 214 (8846), 292 (2160), with base, 230 (9360), 311 (2184), $^1$H-NMR δ ($CHCl_3$): 3.92 (3H, s, $OCH_3$), 5.90 (2H, s, $OCH_2$), 6.33, 6.42 (each 1H, d, J=8.5 Hz, H-4, H-5); HRMS m/z: 168.0422 ($M^+$, 100, $C_8H_8O_4$), 153.0187 ($M^+$ —$CH_3$, 100, $C_7H_5O_4$). This phenol (6 g), $K_2CO_3$ (40 g) and dry acetone (250 ml) were stirred (10 min.) and allylbromide (8 ml) added and refluxed (18 hr). The resulting product on purification produced a colourless liquid (8 g) (3), IR $\nu^{max}_{liq.film}$ $cm^{-1}$: 1620, UV $\nu^{max}_{MeOHJ}$ nm (ε): 215 (9606), 288.6 (2002), no base shift; $^1$H-HMR δ ($CDCl_3$): 3.80 (3H, s, $OCH_3$), 4.70 (2H, d, J=6 Hz, $CH_2$), 5.31 (2H, dd, J=13, 6 Hz, CH=$CH_2$), 5.90 (2H, s, $OCH_2O$), 6.03 (1H, m, $CH_2$=CH), 6.32 (1H, d, J=8.7 Hz, C-5), 6.46 (1H, d, J=8.7 Hz, C-6); HRMS m/z: 208.0735 ($M^+$, 100, $C_{11}H_{12}O_4$), 193.0500 ($M^+$ —$CH_3$, 22; $C_{10}H_9O_4$), 168.0344 ($M^+$ —$CH_2CH$=$CH_2$, 78 $C_8H_7O_4$).

6-Methoxy-2,3-Methylenedioxy,4-Allyl Phenol (4)

Compound (3) (3.5 g) was heated under argon at 195 (1½ hr), cooled, dissolved in ether (200 ml) and extracted with 2N NaOH (250 ml). The NaOH portion was back-washed once with ether, acidified with 6N HCl and extracted with ether (3×250 ml). The ether layer was washed with $NaHCO_3$, followed by water, dried over anhydrous $MgSO_4$, and evaporated to dryness. The resulting product (4) recrystallized from hexane (2.7 g) was a low melting solid having an mp of 52°-53° C.; IR $^{max}{}_{KBr}$ cm$^{-1}$: 1625, 3500; UV $^{max}{}_{MeOH}$ nm ($\epsilon$): 212 (9627), 295 (1782), with base, 219 (11291), 312 (2377); $^1$H-NMR (CDCl$_3$): 3.27 2H, d, J=6 Hz, benzylic CH$_2$), 3.82 (3H, s, OCH$_3$), 5.06 (2H, m, CH=CH$_2$), 5.34 (1H, bs, exchanged with D$_2$O, phenol), 5.90 (2H, s, OCH$_2$O), 5.94 (1H, m, CH$_2$=CH), 6.15 (1H, s, C-6); HRMS m/z- 208.0735 (M+, 100, C$_{11}$H$_{12}$O$_4$). This is the nor methyl-homolog of compound 5 (below), the compound pseudo-dillapiole.

4,5-Dimethoxy,2,3-Methylenedioxy,1-Allyl Benzene (5)

The allyl phenol (4) (1 g) was methylated, as described above, and the product (5) was a colourless liquid (1 g), IR$^{max}{}_{liqfilm}$ cm$^{-1}$: 1610, 1630; UV $^{max}{}_{MeOH}$ nm ($\epsilon$): 216 (10113), 220 (10189), 289 (2077), no base shift; $^1$H-NMR (CDCl$_3$): 3.24 (2H, d, J=6 Hz, benzylic CH$_2$), 3.76 (3H, s, OCH$_3$): 3.94 (3H, s, OCH$_3$), 5.05 (2H, unresolved doublets, CH=CH$_2$), 5.87 (2H, s, OCH$_2$O), 5.93 (1H, m, CH$_2$=CH), 6.14 (1H, s, C-6); $^{13}$C NMR ppm (CDCl$_3$): 58.08 and 56.33 (both q, OCH$_3$), 100.71 (t, OCH$_2$O), 32.97 (t, benzylic CH$_2$), 115.43 (t, CH=CH$_2$), 135.0 (d, CH=CH$_2$), 104.90 (d, C-69, 113.30 (s, C-1), 146.82 (s, C-2), 140.37 (s, C-5), 137.19 (s, C-3), 131.97 (s, C-4); HRMS m/z: 222.0892 (M+, 100, C$_{12}$H$_{14}$O$_4$), 207.0657 (M+ —CH$_3$, 46, C$_{11}$H$_{11}$O$_4$), 195.0576 (M+ —C$_2$H$_3$, 6, C$_{10}$H$_{11}$O$_4$). This is pseudo-dillapiole.

EXAMPLES 2-12

Determination of Biological Activity

In the following examples, the pseudo-dillapiole and its nor homolog were tested at various concentrations for the ED$_{50}$ level by the dilution method in nutrient agar or suspension medium. The test organisms were: The fungi *Cladosporium herbarum* (herein CH), *Helminthosporium carbonum* (HC), *Alternaria brassicicola (AB), Pyrenochaeta terrestris* (PT), and *Alternaria crysanthemia* (AC); bacteria *Xanthomonas campestris pv. campestris* (XC campestris), *Xanthomonas campestris pv. carotae* (XC carotae), *Agrobacterium tumefaciens* (AT), *Rhizobium japonicum* (RJ); and yeast *Saccharomyces cerevisiae* from Universal Foods (yeast I), and haploid lab strain from Yeast I (Yeast II).

For *Xanthomonas campestris* bacteria, the enriched nutrient medium (ENM) used was made by mixing 0.5% glucose and 1.5% commercial nutrient agar. The Wantanabe broth used for bacterial suspension was made up with 0.1% L-glutamic acid, 0.05% L-methionine, 0.3% (NH$_4$)$_2$HPO$_4$, 0.2% KH$_2$PO$_4$, 0.1% MgCl$_2$.6H$_2$O, 0.0001% FeSO$_4$.7H$_2$O, 0.000075% MnSO$_4$.H$_2$O and 0.5% sucrose, and the pH was adjusted to 6.5-7.0. The *Agrobacterium tumefaciens* was assayed in Luria-Bertani (LB) medium containing trylone 1%, yeast extract 0.5%, NaCl 1% and NaOH. 01%. *Rhizobium japonicum* was assayed in yeast—mannitolmedium containing 0.05% NaCl, 0.01% yeast extract, 0.02% K$_2$HPO$_4$, 1% Mannitol and 0.2% concentrated salt solution (the concentrated salts were 0.1 g MgSO$_4$.7H$_2$O, 0.02 g FeCl$_3$, 0.04 g CaCl$_2$, 0.83 ml HCl and 99.0 ml H$_2$O), and the pH was adjusted to 7.2. The medium for yeast contained yeast extract 1%, bacto-peptone 2%, adenine (1 mg/ml) 25% by vol., uracil (1 mg/ml) 2% by vol, agar 2%, and glucose (50%) 4% by vol. The V-8 medium for fungi consisted of V-8 juice (200 ml), CaCO$_3$ (3.0 g) and agar (15.0 g) per 1000 ml medium, and the pH adjusted to 7.2. All the cultures were incubated at 27 for 3-7 days.

Determining of ED$_{50}$ on fungi

ED$_{50}$ values for the fungi were calculated by determining inhibition of mycelial growth on solid nutrient medium (V-8 juice agar). A small plug of the desired fungus on solid nutrient agar, was placed on solid nutrient agar previously incorporated with the compounds under investigation. The concentrations used were from 5 ppm to 100 ppm. The inhibition of the mycelial growth was recorded at the end of 72 hrs.

Determining of ED$_{50}$ on bacteria and yeast

Bacterial and yeast bioassay were carried out in their respective liquid nutrient medium. The compound to be assayed was inoculated with the desired bacteria or yeast and was shaken on a rotary shaker at 170 ppm (28 C) for two days. The samples were visually examined or by measuring the absorbance at 640 nm using a UV-visible spectrophotometer. For a bacterial solution, at 600 nm, an OD value of 0.685 indicates 129×10$^4$ colony forming units (CFU). Before inoculation, each bacteria/yeast in their respective liquid nutrient-medium were diluted to approximately 10$^4$ CFU per ml. 1 ml aliquots of this clear bacterial/yeast solution were used to inoculate the various concentrations of the compound being tested, and at the end of 2 days shaking, activity was recorded by the turbidity of the solution. A clear solution indicated the inhibition. For lower concentrations of the test compounds, after the two days inoculation, aliquots were further diluted with the respective medium; 10 μl of these diluted solutions were applied on solid ENM medium and the number of colony forming units were counted.

The antimicrobial activity of compounds of this invention is represented in Tables I and II below. Prior to these determinations, a preliminary assay was carried out using *Cladosporium herbarum* on TLC plates [4]. The compounds of this invention showed total inhibition at the 5 μg level during TLC assay.

TABLE I

| Antifungal activity shown as ED$_{50}$ concentration in ppm. | | | | | |
|---|---|---|---|---|---|
| | EXAMPLES | | | | |
| Compound | 2 CH | 3 HC | 4 AB | 5 PT | 6 AC |
| 4 = Nor Homolog | 16.5 | 18 | 8 | 10 | 10 |
| 5 = Pseudo-dillapiole | 16.0 | 16 | 8 | 10 | 10 |

CH = *Cladosporium herbarum*
HC = *Helminthosporium carbonum*
AB = *Alternaria brassicicola*
PT = *Pyrenochaeta terrestris*
AC = *Alternaria chrysanthemi*

TABLE II

| Antibacterial yeast activity shown as ED$_{50}$ concentration in ppm. | | | | | |
|---|---|---|---|---|---|
| | EXAMPLES | | | | |
| Compound | 7 X.C. pv. campestris | 8 X.C. pv. carotae | 9 AT | 10 RJ | 11 Yeast-I | 12 Yeast-II |
| 4 = Nor Methyl | | | | | | |

TABLE II-continued

Antibacterial yeast activity shown as $ED_{50}$ concentration in ppm.

| | EXAMPLES | | | | | |
|---|---|---|---|---|---|---|
| | 7 | 8 | 9 | 10 | 11 | 12 |
| Compound | X.C. pv. campestris | X.C. pv. carotae | AT | RJ | Yeast-I | Yeast-II |
| Homolog | 10 | 10 | >200 | >500 | >500 | >500 |
| 5 = Pseudo-dillapiole | 10 | 10 | >200 | >500 | >500 | >500 |

XC = *Xanthomonas campestris*
AT = *Agrobacterium tumefaciens*
RJ = *Rhizobium japonicum*
Yeast-1 = *Saccharomyces cerevisiae* from Universal Foods
Yeast II = haploid PCRI lab strain from Yeast-1.

DISCUSSION

Table I shows the growths of *C. herbarum* (saprophyte), *H. carbonum* (maize pathogen), *A. brassicicola* (cabbage pathogen), *P. terrestris* (onion pathogen) and *A. chrysanthemi* (chrysanthemum sp.) were inhibited by all compounds in the nutrient agar medium at low concentrations. At 50 ppm the compounds totally inhibited the growth of CH and HC. At concentrations more than 20 ppm, the compounds totally inhibited growth of all fungi assayed. The compounds showed total kill at 50 ppm.

Table II, the bacterial and yeast bioassay, showed identical activity for the compounds of the invntion. The yeast were unaffected by the 500 ppm concentration level of the compounds. *A. tumefaciens* and *R. japonicum* suffered growth retardation at concentrations greater than 200 ppm. *X. campestris pv. campestris* (cabbage pathogen) and *pv. carotae* (carrot pathogen) were affected by low concentrations of the compounds.

EXAMPLE 13

Seed Germination Bioassay

A seed germination bioassay test for the compounds was carried out using cress, lettuce, corn and soybean seed. At 250 μg/ml concentrations studied, it was evident that none of the compounds had any effect on the seed germination.

EXAMPLES 14-15

In Vivo Fungicide Screen Evaluation

A series of tests were run to screen for in vivo effectiveness of compounds of the invention. The purpose was to detect activity, and the compounds were applied on plants in greenhouse and growth chamber environments by spray on the foliage at the rate of 100 ppm before the onset of infection by the plant pathogen. The methodology is designed to establish the inter-relationship between host, pathogen and environment necessary to obtain a measure of the test compound's effectiveness. The compounds of the invention were tested in a non-persistent type test for activity as compared to standard commercial fungicides MANCOZEB, BENOMYL, EDIFENPHOS, BAYLETON, FUJI-ONE and ORYZEMATE as reference compounds (see Summary above). Table III shows the results for the compound pseudo-dillapiole (Example 14) and the nor homolog (Example 15):

TABLE III

In Vivo Fungicide Screening Tests
Values expressed as % compared to control at 100 ppm

| | CDM | RB | RSB | TLB | WLR | WPM |
|---|---|---|---|---|---|---|
| Example 14 pseudo-dillapiole (compound 5) | 0 | 0 | 0 | 0 | 0 | 95 |
| Example 15 nor methyl homolog (compound 4) | 0 | 0 | 0 | 0 | 0 | 75 |

CDM = cucumber downy mildew pathogen *Pseudoperonospora cubensis*
RB = rice blast pathogen, *Piricularia oryzae*
RSB = rice sheath blight pathogen *Pellicularia filamentosa*
TLB = tomato leaf blight pathogen *Phytophtora infestans*
WLR = wheat leaf rust pathogen, *Puccinia recondita.*

EXAMPLE 16

Specificity

As noted above the compounds are ineffective as herbicides against one or more of the following weeds: average dicots, cocklebur, morning glory, pigweed, smartweed, velvet leaf, average monocots, barnyard grass, green foxtail, johnson grass, yellow nutsedge and the wild oat in both pre-emergent and post-emergent screening tests, at application rates of 2 lbs/acre for Compound 4, and 4 lbs/acre for Compound 5. Likewise, the compound showed no insecticide activity, measured as effective kill rates at dosages varying between 150 to 600 ppm, against southern armyworm, mexican bean beetle, southern corn rootworm, green peach aphid, two-spitted spider mite, and southern root knot nematode.

Surprisingly, compounds of the invention, particularly pseudo-dillapiole, 4,5-dimethoxy-2,3-methylenedioxy-1-allyl benzene and the nor homolog, are highly specific and selectively active. The bioassay results indicated that the compounds have no significant difference in their activities against the microorganisms studied and in not inhibiting seed germination. Activity on microbes but lack of adverse effect on plants by these compounds is a distinct advantage in their use as antimicrobiol agents. The activity against varieties of *Xanthomonas campestris* bacteria indicates that the compounds of the invention may have particular utility as control agents against the dreaded Citrus Canker disease which is caused by the related *Xanthomonas campestris pv. citrii* bacteria.

The application to plants is preferably foliar, employing a suitable carrier fluid in the range of 5 to 500 ppm, and application prior to the onset of infection (pre-infection) is preferred.

It should be understood that various modifications within the scope of this invention can be made by one of

Citations

1. Dallacker, F., Zur Synthese v on Dimethoxy-methlenedioxy allyl-benzolen. Chem. Ber. 102, 2663–2676 (1969).
2. Devakumar, C., Saxena, V. S., and Mukerjee, S. K., Agri, Biol. Chem. 49 (3): 725 (1985).
3. Indian Patent No. 128,129 (1969), Improvements in or relating to methylenedioxyphenyl derivatives, Issued to The Director, Indian Agricultural Research Institute.
4. A. L. Homans and A. Fuchs, *J. Chromatog.* 51, 327 (1970).

Other Information

5. Burke, B., and Nair, M., Phenylpropene, Benzoic Acid and Flavonid Derivatives from Fruits of Jamaican *Piper* Series, Phytochemistry, Vol. 25, No. 6 pp 1427–1430, June 1986.
6. Nair, M., Thesis, *Chemical and Preliminary Biological Investigation of Some Jamaican Medicinal Plants,* University of the West Indies, Mona, Kingston, Jamaica, May 1984.

We claim:

1. An antimicrobiol composition comprising in operative combination:
   (a) at least one 4,5-substituted-2,3-alkylidenedioxy-1-olefinic benzene;
   (b) said 4,5-substituted-2,3-alkylidenedioxy-1-olefinic benzene being selected from the group consisting of compounds of the formula:

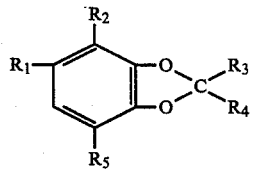

wherein $R_1$ and $R_2$ may be the same or different and are selected from OH and $C_1$–$C_5$ alkoxy (—OR) groups, $R_3$ and $R_4$ are selected from H and $C_1$–$C_5$ alkyl, alkenyl and alkynyl groups, and $R_5$ is selected from $C_3$–$C_7$ alkyl, alkenyl and alkynyl groups, and $R_5$ is not allyl when $R_1$ is methoxy, $R_2$ is OH or methoxy, and $R_3$ and $R_4$ are each H;
   (c) a plant-compatible carrier material;
   (d) said 4,5-substituted-2,3-alkylidenedioxy-1-olefinic benzene being present in association with said carrier material to form a composition; and
   (e) said 4,5-substituted-2,3-alkylidenedioxy-1-olefinic benzene being present in said composition in an amount sufficient to impart anti-microbiol properties thereto, and said carrier material being present as the major component of said composition.

2. An antimicrobiol composition as in claim 1 wherein $R_5$ unsaturation is selected from a terminal double or triple bond.

3. An antimicrobiol composition as in claim 2 wherein $R_1 = R_2$.

4. An antimicrobiol composition as in claim 2 wherein $R_1$ and $R_2$ are different.

5. An antimicrobiol composition as in claim 4 wherein $R_2 =$ OH and $R_1 =$ OCH$_3$.

6. An antimicrobiol composition as in claim 3 wherein $R_1$ and $R_2$ are OCH$_3$.

7. An antimicrobiol composition as in claim 5 wherein $R_3$ and $R_4$ are H.

8. An antimicrobiol composition as in claim 6 wherein $R_3$ and $R_4$ are H.

9. An antimicrobiol composition as in claim 1 wherein said carrier is a fluid.

10. An antimicrobiol composition as in claim 5 wherein said carrier is a fluid.

11. An antimicrobiol composition as in claim 6 wherein said carrier is a fluid.

12. A method of reducing the incidence of attack of plant microbiol pathovars comprising:
    (a) applying to plants before the onset of infection an antimicrobiol composition at a rate of from about 5 to 500 ppm;
    (b) said antimicrobiol composition comprising in operative combination:
        (i) at least one 4,5-substituted-2,3-alkylidenedioxy-1-olefinic benzene in an antimicrobially sufficient amount in association with a carrier material for application to plants; and
        (ii) said 4,5-substituted-2,3-alkylidenedioxy-1-olefinic-benzene being selected from the group consisting of compounds of the formula:

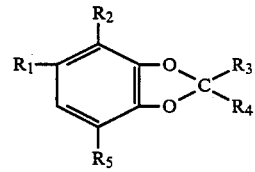

wherein $R_1$ and $R_2$ may be the same or different and are selected from OH and $C_1$–$C_5$ alkoxy (—OR) groups, $R_3$ and $R_4$ are selected from H and $C_1$–$C_5$ alkyl, alkenyl and alkynyl groups, and $R_5$ is selected from $C_3$–$C_7$ alkyl, alkenyl and alkynyl groups.

13. A method of reducing the incidence of attack of plant microbial pathovars as in claim 12 wherein $R_1 =$ OCH$_3$, $R_2 =$ OH, $R_3$ and $R_4$ are H, and $R_5$ is allyl in said antimicrobial composition.

14. A method of reducing the incidence of attack of plant microbial pathovars as in claim 12 wherein $R_1$ and $R_2$ are OCH$_3$, $R_3$ and $R_4$ are H, and $R_5$ is allyl in said antimicrobial composition.

15. A method as in claim 12 comprising foliar application in the form of a liquid carrier containing said composition.

16. A method as in claim 13 comprising foliar application in the form of a liquid carrier containing said composition.

17. A method asin cliam 14 comprising foliar application in the form of a liquid carrier containing said composition.

18. An antimicrobial composition comprising in operative combination:
    (a) at least one 4,5-substituted-2,3-alkylidenedioxy-1-olefinic benzene;
    (b) said 4,5-substituted-2,3-alkylidenedioxy-1-olefinic-benzene being selected from the group consisting of compounds of the formula:

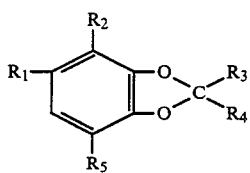

wherein $R_1$ and $R_2$ may be the same or different and are selected from OH and $C_1$–$C_5$ thioalkyl (—SR) groups, $R_3$ and $R_4$ are selected from H and $C_1$–$C_5$ alkyl, alkenyl and alkynyl groups, and $R_5$ is selected from $C_3$–$C_7$ alkyl, alkenyl and alkynyl groups;

(c) a plant-compatible carrier material;

(d) said 4,5-substituted-2,3-alkylidenedioxy-1-olefinic benzene being present in assocation with said carrier material to form a composition; and (e) said 4,5-substituted-2,3-alkylidenedioxy-1-olefinic benzene being present in said composition in an amount sufficient to impart anti-microbial properties thereto, and said carrier material being present as the major component of said composition.

* * * * *